(12) United States Patent
Roberts et al.

(10) Patent No.: US 6,492,132 B1
(45) Date of Patent: Dec. 10, 2002

(54) CYTOCHROME P450 ELECTROCHEMICAL SYSTEM

(75) Inventors: Gordon Roberts, Bruntingthorpe (GB); Andrew Abbott, Leicester (GB); Paul Cullis, Leicester (GB); Farjad Ahmed, London (GB); William Primrose, Glasgow (GB)

(73) Assignee: University of Leicester, Leicester (GB)

( * ) Notice: Subject to any disclaimer, the term of this patent is extended or adjusted under 35 U.S.C. 154(b) by 0 days.

(21) Appl. No.: 09/807,059

(22) PCT Filed: Oct. 8, 1999

(86) PCT No.: PCT/GB99/03337
§ 371 (c)(1),
(2), (4) Date: Apr. 6, 2001

(87) PCT Pub. No.: WO00/22158
PCT Pub. Date: Apr. 20, 2000

(30) Foreign Application Priority Data

Oct. 9, 1998 (GB) .............................................. 9821932

(51) Int. Cl.⁷ ............................ C12Q 1/26; C12M 1/34; C12M 1/00
(52) U.S. Cl. ...................... 435/25; 435/817; 435/283.1; 435/287.1
(58) Field of Search ....................... 435/25, 817, 283.1, 435/287.1

(56) References Cited

U.S. PATENT DOCUMENTS

| | | | |
|---|---|---|---|
| 4,318,784 A | * 3/1982 | Higgins et al. | ................ 204/73 |
| 4,541,908 A | 9/1985 | Niki et al. | |
| 4,655,885 A | 4/1987 | Hill et al. | |
| 5,413,915 A | 5/1995 | Case et al. | |

FOREIGN PATENT DOCUMENTS

GB 2312960 A 8/1997

OTHER PUBLICATIONS

Kazlauskaite et al, Direct electrochemistry of cytochrome P450cam, Chem. Commun., 1996, pp. 2189–90 1996, Cambridge XXP000867499.

European Patent office, International Preliminary Examination Report, 9 pages total, PCT/GB99/03337 Dec. 1, 2000; Munich Germany.

Reipa, V. and Vilker, V.L., Effic. Process.: Electrochem. Technol. Synth., Sep., Recycle, Environ. Improv., Int. Forum, Electrolysis Chem. Ind., $12^{th}$ (1998) (Abstract). 1998, Lancaster, NY (XP–002129730).

Archakov, A.I., et al, Dokl. Acad. Nauk. SSSR (1981) 258(1) (Abstract). 1981, Moscow, Russia ISSN 0002–3264; (XP002129731).

Iwuoha, E.I. et al, Drug metabolism biosensors: electrochemical reactivities of cytochrome $P450_{cam}$ immobilised in synthetic vesicular systems, J. Phar. & Biomed. Anal., 17(1998) 1101–1110 1998, US PMID: 9884200 (XP–000874063).

Sugihara, N. et al, Immobilization of Cytochrome P–450 and Electrochemical Control of its Activity, Polym. Adv. Technol., 9(1998) 307–313 1998, US (XP–000768598).

Kazlauskaite, J., et al, Chem. Commun., (18) 2189–2190 1996, Cambridge, England (XP–000867499).

Vilker, V.L., et al, Bacterial Cytochrome P–450 Enzymes and Reactions on Immobilized Electrodes, Proc. Int. Symp. Redox Mech. Interfacial Prop. Mol. Biol. Importance, $3^{rd}$ (1988) 105–112 1988, US (XP–000874489).

Vilker, V.L. and Wong, L.S. Synthesis of Oxygenated Hydrocarbons by Cytochrome P450 Electroenzymology, Electrochem. Soc. Proc., V. 97–6, 91–99. 1997, US (XP–000874026).

Jin W. et al, J. Electroanal. Chem. (1997) 433(1–2) (Abstract) 1997, US (XP–002129732).

* cited by examiner

*Primary Examiner*—Louise N. Leary
(74) *Attorney, Agent, or Firm*—Dority & Manning, PA

(57) ABSTRACT

The present invention concerns class II cytochrome P450s, electrochemical systems for assaying cytochrome P450 catalytic activity, apparatus and methods for same.

15 Claims, No Drawings

CYTOCHROME P450 ELECTROCHEMICAL SYSTEM

The present invention concerns class II cytochrome P450s, electrochemical systems for assaying cytochrome P450 catalytic activity, apparatus and methods for same.

Cytochromes P450 constitute a large family of haem thiolate enzymes, found in bacteria, fungi, plants, insects and animals, which catalyse a wide range of reactions, including hydroxylation of aliphatic & aromatic carbons, epoxidation, oxidative deamination, sulphoxide formation, N-oxidation, N-hydroxylation, dehalogenation and N-, O- and S-dealkylation. These diverse reactions all arise from the fact that cytochromes P450 are versatile oxygen-activation catalysts which incorporate one atom of molecular oxygen into a broad range of substrates with concomitant reduction of the other oxygen atom to water. These enzymes play important roles in the biosynthesis of secondary metabolites in plants, in steroid metabolism in fungi and animals and, notably, in xenobiotic metabolism.

The considerable diversity of P450s results in man being able to metabolize a wide range of foreign chemicals. Metabolism by P450s has a major influence on the pharmaco-toxicological properties of therapeutic drugs, and consideration of this metabolism is a key part of the drug design process. Furthermore, several P450s are polymorphic in the human population, resulting in individual differences in drug and toxin metabolism. In a different sphere, the ability of cytochromes P450 to hydroxylate unactivated carbons suggests that they have potential applications in synthetic chemistry.

In vivo, P450s require other proteins as electron donors. The class I enzymes (most bacterial P450s, and the mitochondrial steroid-metabolising enzymes) require an NADH-dependent reductase and an iron-sulphur protein, while the class II enzymes (e.g. the mammalian drug-metabolising enzymes) simply require a flavoprotein NADPH-dependent reductase. The mammalian drug-metabolising monooxygenase system thus consists of NADPH-cytochrome P450 reductase and a number of different P450s, all of which are bound to the membranes of the endoplasmic reticulum. (By contrast, the only known bacterial class II P450, P450 BM3 (CYP102) from *Bacillus megaterium*, is a soluble enzyme having both P450 and NADPH-cytochrome P450 reductase activities in a single polypeptide chain.)

The assay of cytochromes P450, for example to study the metabolism of a new therapeutic agent, has classically involved incubation of the candidate substrate with a microsomal membrane preparation from the cells of interest, together with NADPH as an electron source, followed by chromatographic analysis for product formation. Because several different P450s are expressed in most cell types, it is difficult in this kind of assay to identify the specific P450(s) responsible for metabolism of the compound of interest.

More recently, therefore, individual recombinant P450s expressed in bacteria, yeast, insect or mammalian cells (see, for example Gonzalez, F. J. et al., 1995, Ann. Rev. Pharmacol. Toxicol., 36: 369–390; Pritchard, M. P. et al., 1997, Arch. Biochem. Biophys. 345: 342–354; Guengerich, F. P. et al., 1997, Curr. Opin. Biotechnol., 8: 623–628) have been used in combination with endogenous or recombinant P450 reductase. These assays have generally also involved chromatographic analysis; while NADPH consumption can be followed spectrophotometrically, the coupling between electron flow and product formation is variable and hence NADPH consumption may not be a reliable indicator of metabolism of a given compound.

It has recently been shown that electrons can be supplied to P450 reductase electrochemically from a platinum electrode by means of a mediator, cobalt sepulchrate (Estabrook, R. W. et al., Meth. Enzymol., 272: 44–51), and on the basis of this systems have been developed in which fusion proteins comprising NADPH-cytochrome P450 reductase and a class II cytochrome P450 can be driven electrochemically (Estabrook, R. W. et al, 1996, Endocrine Res., 22: 665–671). In the case of the quite different class I P450s, it has recently been shown that electrons can be supplied electrochemically either via putidaredoxin (Reipa, V. et al., 1997, PNAS USA, 94: 13554–13558) or directly to the P450 if the latter is immobilised in a lipid film (Zhang, Z. et al., J. Chem. Soc. Faraday Trans., 93; 1769–1774).

Further examples of prior art systems involving the use of Class I P450 enzymes such as P450cam are given in Kazlauskaite, J. et al. (1996, Chem. Commun (Cambridge), 18: 2189–2190), Vilker, V. L. et al. (Redox Chem. Interfacial Behav. Biol. Mol., 1987, 105–112), Vilker, V. L. et al. (1997, Proc. Electrochem. Soc., Volume 97-6: 91–99) and GB 2312960.

The present invention overcomes the prior art disadvantages, particularly those associated with the use of a P450 reductase to supply electrons to a P450, and provides simple and convenient methods and arrangements for supplying electrons to class II cytochromes P450, particularly for assaying P450 catalytic activity.

Although it has not previously been possible to supply electrons to P450 cytochromes without the use of P450 reductases, the present invention obviates this need.

Thus according to the present invention there is provided a class II cytochrome P450 attached to a graphite electrode. In contrast to the prior art this attachment does not require P450 reductase and thus provides a substantial advantage over the prior art.

The P450 cytochrome is attached such that upon catalysis of a reaction by the enzyme, electron flow occurs from the electrode to the enzyme.

The P450 cytochrome may be attached to the electrode via dodecyl dimethylammonium bromide (DDAB). It may be attached via other amphiphilic molecules which are insoluble in aqueous solutions. Such molecules are well known and will be readily apparent to one skilled in the art. They include Nafion (RTM) and phosphatidylcholine.

Also provided according to the present invention is apparatus for determining the catalytic activity of a class II P450 cytochrome, comprising a cell having a graphite electrode having attached to it the cytochrome P450, and also having electron flow detection means.

The inventors have also found that it is not necessary for the P450 cytochrome to be bound to an electrode, and thus also provided according to the present invention is apparatus for detecting the catalytic activity of a class II P450 cytochrome comprising a cell having a modified gold electrode contacting a solution containing the enzyme.

The gold electrode may be coated in 2,2-dithiodipyridine (Adrithiol) or by other polyfunctional molecules which can be adsorbed onto the electrode and also interact specifically with the cytochrome P450. These molecules will be readily apparent to one skilled in the art, and include those compounds disclosed as "mediators" by Christensen, P. A. and Hamnett, A. ("Techniques and Mechanisms in Electrochemistry", 1994, Blackwell Academic Press, London, pp. 356–373) which is incorporated herein by reference in its entireity. The polyfunctional molecules may have the structure of "Type IV" compounds discussed by Christensen and Hamnett (supra) and Allen, P. M. et al., 1984, J. Electroanal. Chem., 178: 69 which is incorporated herein by reference in its entireity. The compounds may include 1,2 bis(4-pyridyl) ethylene, 4,4' bipyridine, bis (4-pyridyl) bisulphide, or 4 mercaptopyridine. Such modified gold electrodes are able to supply electrons to the cytochrome P450 yet do not need to be attached by strong chemical bonds to the cytochrome P450.

Compounds suitable to act as mediators of electron flow from and electrode to an enzyme are also disclosed by R. W. Murray (Acc. Chem. Res., 1980, 13, 135) which is incorporated in its entireity herein by reference.

Generally speaking, cells may be three-electrode cells having a first electrode as described above (i.e. graphite or gold) and second and third electrodes comprising a saturated calomel working electrode and a platinum wire counter-electrode. Naturally, each electrode should contact the solution to be tested for the presence of a substrate for the P450 cytochrome.

The electron flow detection means may monitor current flow or may determine a steady state cyclic voltammogram, for example over the range −0.4V to +0.4V.

The cytochrome P450 catalytic activity may also result in the generation of peroxides, essentially a side-product when it is desired to assay the generation of a specific product resulting from catalysis. The generation of peroxides results in electron flow and thus affects the results obtained by the apparatus. Thus the apparatus may additionally comprise means for detecting peroxide formation. Such means are well known and include colourimetric peroxide assay means and fluorimetric peroxide assay means. Alternatively, it may comprise an electrode which detects peroxide. Thus the electron flow required for the assayed peroxide generation can be subtracted from the total electron flow and a more accurate measure of product formation obtained.

A range of applications exists for the present invention, particularly for the screening of novel compounds as substrates to a cytochrome P450 and for the use of P450 catalysis in synthetic chemistry. For example a high-throughput screening system for P450 substrates could be readily created. In the case of using P450s for synthetic chemistry, the ability of P450s to catalyse hydroxylation of unactivated carbons, together with their broad substrate specificity, makes them attractive tools for synthetic chemistry. However, the high cost of NADPH has to date hampered this. The ability of the present invention to drive reactions electrochemically now makes their use more commercially attractive.

Thus the present invention also provides a method of determining the catalytic activity of a class II cytichrime P450, comprising the use of apparatus according to the present invention. It may be a method for determining whether a given compound is a substrate for a class II cytochrome P450.

Also provided is a method of performing a synthetic chemical reaction, comprising the use of apparatus according to the present invention.

The invention will be further apparent from the following description, which shows, by way of example only, forms of electrochemical assays.

Experimental

Cytochromes P450 BM3 and P450 3A4 were expressed and purified as described below. Electrochemical assays were performed using both enzyme immobilised on a graphite electrode and also enzyme in solution with a modified gold electrode. The results showed that they were accurate assays for P450 catalytic activity.

Expression and Purification of Cytochromes P450

A number of different procedures have been described for the purification of recombinant cytochromes P450 from different sources. The procedures used to obtain the proteins used in the present work are described briefly by way of illustration; any other expression and purification procedure which yields pure solubilised recombinant P450s would be equally satisfactory. The expression and purification of B. megaterium P450 BM3 has been published (Modi, S. et al., 1995, Biochemistry, 34: 8982–8988), and is therefore only summarised briefly; the purification of human P450 3A4 is not yet published and is therefore given in more detail.

*B. megaterium* cytochrome P450 BM3

The *E. coli* plasmid pJM20, encoding the expression system for the haem (P450) domain of cytochrome P450 BM3, described in (Miles, J. S. et al., 1992, Biochem. J., 288: 503–509), was obtained. The host strain used was *E. coli* XL Blue 1 (supE44, hsdR17, recA1, endA1, gyrA46, thi, relA1, lac−F' [proAB+lacI$^q$ lacZDM15 Tn10 (tet$^r$)]). The expression and purification of the protein has previously been described. The transformed cells were grown in Terrific Broth medium containing 50 μg/ml ampicillin and 50 μg/ml IPTG. The cells were harvested by centrifugation at 10,000 rpm for 15 minutes and the resuspended cells broken by passage twice through a French Press (2.5 cm id×17 cm, Power Laboratory Press, American Instrument Co. Inc.). Cell lysates were fractionated by ammonium sulphate precipitation, followed by ion exchange chromatography on a DEAE Sephacel (Pharmacia LKB) column, by chromatography on a hydroxyapatite column (Bio-Rad) and, finally, by gel filtration on a Sephacryl S300 (Pharmacia LKB) column. This resulted in homogenous active protein as shown by SDS-PAGE (with Coomassie blue staining), by electrospray mass spectrometry, by the ratio of absorbance at 418 nm and 280 nm (where a ratio of >1.7 is characteristic of pure protein), and by the absence of any absorbance band at 420 nm in the CO complex of the reduced enzyme. Protein concentrations were measured by the method of Omura and Sato (1964, J. Biol. Chem., 239: 2379–2387) using a value of $\epsilon = 77.5$ mM$^{-1}$ cm$^{-1}$ at 418 nm.

Human Cytochrome P460 3A4

The *E. coli* plasmid pCW-3A4ompAhis6, encoding the expression system for human cytochrome P450 3A4, described by Pritchard, M. P. et al.,(1997, Arch. Biochem. Biophys., 345: 342–354), was obtained. The host strain used was *E. Coli* JM109 (Promega). 10–12 single colonies of *E. coli* JM109 transformed with the plasmid pCW-3A4ompAhis6 were picked from a freshly streaked plate and inoculated into 50 ml Modified Terrific Broth (per liter: 12 g, 24 g yeast extract, 2 g peptone, 4 ml glycerol, 17 mM potassium di-hydrogen orthophosphate, 72 mM di-potassium hydrogen orthophosphate) supplemented with 1 mM thiamine, trace elements (6.1 mg/l iron (III) citrate, 0.43 mg/l zinc chloride, 0.5 mg/l cobalt chloride, 0.5 mg/l disodium molybdate, 0.25 mg/l calcium chloride, 0.32 mg/l copper chloride acidified with 0.13 mg/l boric acid and 25 μl concentrated hydrochloric acid), 50 μg/ml ampicillin and 1 mM δ-aminolevulinic acid, in a 250 ml flask. Cultures were grown at 37° C. in a shaking incubator until reaching an OD at 600 nm of 0.6, at which point isopropylthio-β-D-galactopyranoside (Gibco) was added to a final concentration of 1 mM, and the cultures were grown on for 20 hours in a shaking incubator at 30° C.

Cultures were transferred to 50 ml Fulcrum tubes and cooled on ice for 15 minutes prior to pelleting the cells (20 minutes at 3000 rpm, 2800 g, Sorvall RT7 centrifuge). The cells were resuspended in 5 ml 2×TSE buffer (100 mM Tris-acetate, 500 mM Sucrose, 0.5 mM EDTA, pH 7.6), diluted with 5 ml sterile water after resuspension. Lysozyme was added from a fresh 10 mg/ml aqueous solution to a concentration of 0.25 mg/ml and the cells swirled gently for 46 minutes at 4° C. The spheroplasts were spun down (20 minutes, 3000 rpm, Sorvall RT7 Centrifuge), the supernatant discarded and resuspended in 100 mM potassium phosphate, 6 mM magnesium acetate, 20% v/v glycerol, 0.1 mM dithiothreitol, pH 7.6. Phenylmethyl sulphonyl fluoride (PMSF) was added to 1 mM and the cells were lysed by sonication (SGE Soniprep, 4×20 sec bursts, full power). Cell debris was spun down (20 minutes, 3000 rpm, Sorvall RT7 Centrifuge) and Emulgen 911 was added (0.1% v/v final concentration, 10% v/v aqueous stock). The detergent/lysate solution was swirled at 4° C. for 45 minutes before pelleting the insoluble material by ultracentrifugation (Sorvall Ultra Pro 80 ultracentrifuge, 60 minutes, 180,000 g, 4° C.).

A 1 ml Hi-Trap Agarose column was charged with 2 ml 100 mM nickel sulphate and washed with buffer A (20 mM potassium phosphate, 600 mM potassium chloride, 20% v/v glycerol, pH 7.4). The solubilised lysate solution was passed down the column which was then washed with 5 column volumes buffer A then 10 column volumes of buffer A containing 75 mM imidazole. The purified protein was eluted with buffer A containing 1 M imidazole, the eluate being clearly identifiable by its intense red colour. The protein solution was diluted 20-fold in buffer A and dialysed in prewashed EDTA-treated dialysis tubing against 2 L of buffer B (20 mM potassium phosphate, 0.2 mM DTT, 1 mM EDTA, 1 mM benzamidine, 0.05% Emulgen 911, 60 mg/ml PMSF, pH 7.0) and loaded on to a Mono S (Pharmacia) column. The column was washed with 60 ml of buffer B and the P450 3A4 was eluted with a linear salt gradient (0 to 0.2 M KCl) in buffer B. This resulted in homogenous active protein, as shown by SDS-PAGE (with Coomassie blue staining), by the ratio of absorbance at 418 mn and 280 nm, and by the absence of any absorbance band at 420 nm in the CO complex of the reduced enzyme. Protein concentrations were measured by the method of Omura and Sato (supra).

Electrochemical Assay Systems

Two different methods have been developed for electrochemical assay of P450s

Use of Enzyme Immobilised on a Graphite Electrode.

A graphite working electrode (0.2 cm$^2$ surface area) was prepared by polishing first with 1 μm and then with 0.3 μm alumina powder. A surfactant coating was then cast onto the graphite surface by applying 10 μl of 0.1 M didodecyldimethylammonium bromide (DDAB) in dichloroethane; the dichloroethane was evaporated gradually overnight. The DDAB-graphite electrode was then coated with protein by placing it in a solution of 30 μM cytochrome P450 in 0.1 M potassium phosphate buffer, pH 8.0, for 2 hours.

A three-electrode cell was used, employing a saturated calomel working electrode, a platinum wire counter electrode and the enzyme-DDAB-graphite working electrode. The solution in the cell was 0.1 M potassium phosphate buffer, pH 8.0. The potential was scanned between the limits +0.4 to −0.4 V vs. SCE until a steady state cyclic voltammogram was obtained. A blank current was obtained by scanning the potential between the above limits at 0.1 V s$^{-1}$; three scans were averaged, and the current at the minimum of the cyclic voltammogram was measured. The experiment was then repeated in the presence of substrate (typically 1 mM), and the difference between the current at the minimum of the cyclic voltammogram in the presence and absence of substrate was taken as the assay reading.

Use of a Modified Gold Electrode

A gold electrode (0.031 cm$^2$ surface area) was modified by placing it in a solution of 0.1 M Adrithiol (2,2'-dithiodipyridine) in dichloroethane overnight. The dichloroethane was allowed to evaporate by standing the electrode in air for 10 minutes.

A three-electrode cell was used, employing a saturated calomel working electrode, a platinum wire counter electrode and the modified gold working electrode. The solution in the cell was 0.1 M potassium phosphate buffer, pH 8.0, containing, typically, 20 μM enzyme. The potential was scanned between the limits +0.4 to −0.4 V vs. SCE until a steady state cyclic voltammogram was obtained. A blank current was obtained by scanning the potential between the above limits at 0.1 V s$^{-1}$; three scans were averaged, and the current at the minimum of the cyclic voltammogram was measured. The experiment was then repeated in the presence of substrate (typically 1 mM), and the difference between the current at the minimum of the cyclic voltammogram in the presence and absence of substrate was taken as the assay reading.

When it was desired to accumulate sufficient products for analysis, the experiment was run as described, using either type of electrode, except that the potential was maintained at a fixed value within the above limits for the necessary time period. The electrodes were then removed and the products extracted from the reaction mixture with ethyl acetate. After evaporation of the ethyl acetate the products were separated by HPLC and analysed by gas chromatography—mass spectrometry and/or nuclear magnetic resonance spectroscopy. These analyses demonstrated that the same products were obtained from the electrochemical assay as from the conventional assay employing NADPH and NADPH-cytochrome P450 reductase.

What is claimed is:

1. A class II cytochrome P450 enzyme attached to a graphite electrode.

2. A class II cytochrome P450 enzyme according to claim 1, wherein said cytochrome P450 enzyme is attached such that upon catalysis of a reaction by said enzyme, electron flow occurs from said electrode to said enzyme.

3. A class II cytochrome P450 enzyme according to either one of claims 1 or 2, wherein said cytochrome P450 enzyme is attached to said electrode via didodecyldimethylammonium bromide (DDAB).

4. A class II cytochrome P450 enzyme according to claim 1, wherein said enzyme is not used in conjunction with P450 reductase.

5. Apparatus for determining the catalytic activity of a class II cytochrome P450 enzyme, comprising a cell having a graphite electrode having attached to it said class II cytochrome P450 enzyme, and also having electron flow detection means.

6. Apparatus according to claim 5, wherein said cytochrome P450 enzyme is attached to said graphite electrode via DDAB.

7. Apparatus for detecting the catalytic activity of a class II cytochrome P450 enzyme, comprising a cell having a modified gold electrode contacting a solution containing said class II cytochrome P450 enzyme.

8. Apparatus according to claim 7, wherein said gold electrode is coated with 2,2-dithiodipyridine.

9. Apparatus according to claim 5, wherein said cell is a three-electrode cell, and said electrodes other than said graphite electrode are a saturated calomel working electrode and a platinum wire counter-electrode.

10. Apparatus according to claim 5 or 7, wherein said electron flow detection means determines a steady state cyclic voltammogram.

11. Apparatus according to claim 5 or 7, additionally comprising peroxide formation detection means.

12. A method of determining the catalytic activity of a class II cytochrome P450 enzyme, comprising the use of apparatus according to claim 5 or 7.

13. A method according to claim 12, wherein it is a method of determining the specificity of said class II cytochrome P450 for a given substrate.

14. A method of carrying out a synthetic chemical reaction, comprising the use of apparatus according to claim 5 or 7.

15. Apparatus according to claim 7, wherein said cell is a three-electrode cell, and said electrodes other than said modified gold electrode are a saturated calomel working electrode and a platinum wire counter-electrode.

* * * * *